(12) United States Patent
Fukuzawa et al.

(10) Patent No.: US 8,506,586 B2
(45) Date of Patent: Aug. 13, 2013

(54) NEEDLE INSERTION DEVICE

(75) Inventors: Masahiro Fukuzawa, Kyoto (JP); Yoshiharu Uehata, Kyoto (JP)

(73) Assignee: Arkray, Inc. (JP)

( * ) Notice: Subject to any disclaimer, the term of this patent is extended or adjusted under 35 U.S.C. 154(b) by 1151 days.

(21) Appl. No.: 10/557,515

(22) PCT Filed: May 20, 2004

(86) PCT No.: PCT/JP2004/006846
§ 371 (c)(1),
(2), (4) Date: Nov. 21, 2005

(87) PCT Pub. No.: WO2004/103178
PCT Pub. Date: Dec. 2, 2004

(65) Prior Publication Data
US 2007/0055297 A1    Mar. 8, 2007

(30) Foreign Application Priority Data

May 21, 2003 (JP) ................. 2003-143194

(51) Int. Cl.
*A61B 17/14* (2006.01)
*A61B 17/32* (2006.01)

(52) U.S. Cl.
USPC ........................................................ 606/181

(58) Field of Classification Search
USPC ................. 606/181–183; 600/573, 578, 583
See application file for complete search history.

(56) References Cited

U.S. PATENT DOCUMENTS

| 4,203,446 | A | * | 5/1980 | Hofert et al. | 606/182 |
|---|---|---|---|---|---|
| 4,328,879 | A | * | 5/1982 | Tone | 180/219 |
| 5,318,583 | A | | 6/1994 | Rabenau et al. | |
| 5,545,174 | A | * | 8/1996 | Schenk et al. | 606/182 |
| 6,045,567 | A | | 4/2000 | Taylor et al. | |
| 6,210,421 | B1 | | 4/2001 | Bocker et al. | |
| 6,231,531 | B1 | * | 5/2001 | Lum et al. | 601/46 |
| 6,858,015 | B2 | * | 2/2005 | List | 600/583 |
| 6,929,649 | B2 | * | 8/2005 | Pugh | 606/182 |
| 7,033,371 | B2 | | 4/2006 | Alden et al. | 606/181 |
| 7,144,404 | B2 | * | 12/2006 | Whitson et al. | 606/181 |
| 7,244,266 | B2 | * | 7/2007 | Garthe et al. | 606/181 |
| 2003/0050573 | A1 | * | 3/2003 | Kuhr et al. | 600/567 |
| 2003/0050656 | A1 | * | 3/2003 | Schraga | 606/182 |
| 2003/0225429 | A1 | | 12/2003 | Garthe et al. | |
| 2004/0092996 | A1 | * | 5/2004 | List et al. | 606/181 |

FOREIGN PATENT DOCUMENTS

| DE | 102 06 254 | * | 1/2003 |
|---|---|---|---|
| JP | 64-42010 | | 3/1989 |
| JP | 6-7329 | | 1/1994 |
| JP | 2000-237172 | | 9/2000 |
| JP | 2001-503284 | | 3/2001 |
| JP | 2003-265447 | | 9/2003 |
| WO | WO 98/06331 | | 2/1998 |
| WO | WO 01/13794 | * | 3/2001 |

* cited by examiner

*Primary Examiner* — Thomas McEvoy
(74) *Attorney, Agent, or Firm* — Studebaker & Brackett PC

(57) ABSTRACT

A lancing device (X) comprising a first moving member (32) holding a lancing member (11) moved from a standby position to a puncturing position in a puncturing direction (N1), for puncturing a target portion by the lancing member (11). The lancing device (X) further comprises a second moving member (31) connected to the first moving member (32), for controlling the movement of the first moving member (32) upon the movement of the second moving member, and also comprises an impact absorbing means (23A) for absorbing impact that is caused when the first and the second moving members (31), (32) come to stop on puncture operation. The impact absorbing means (23A) includes an elastic member (23Ab) for absorbing impact by elastic deformation.

17 Claims, 15 Drawing Sheets

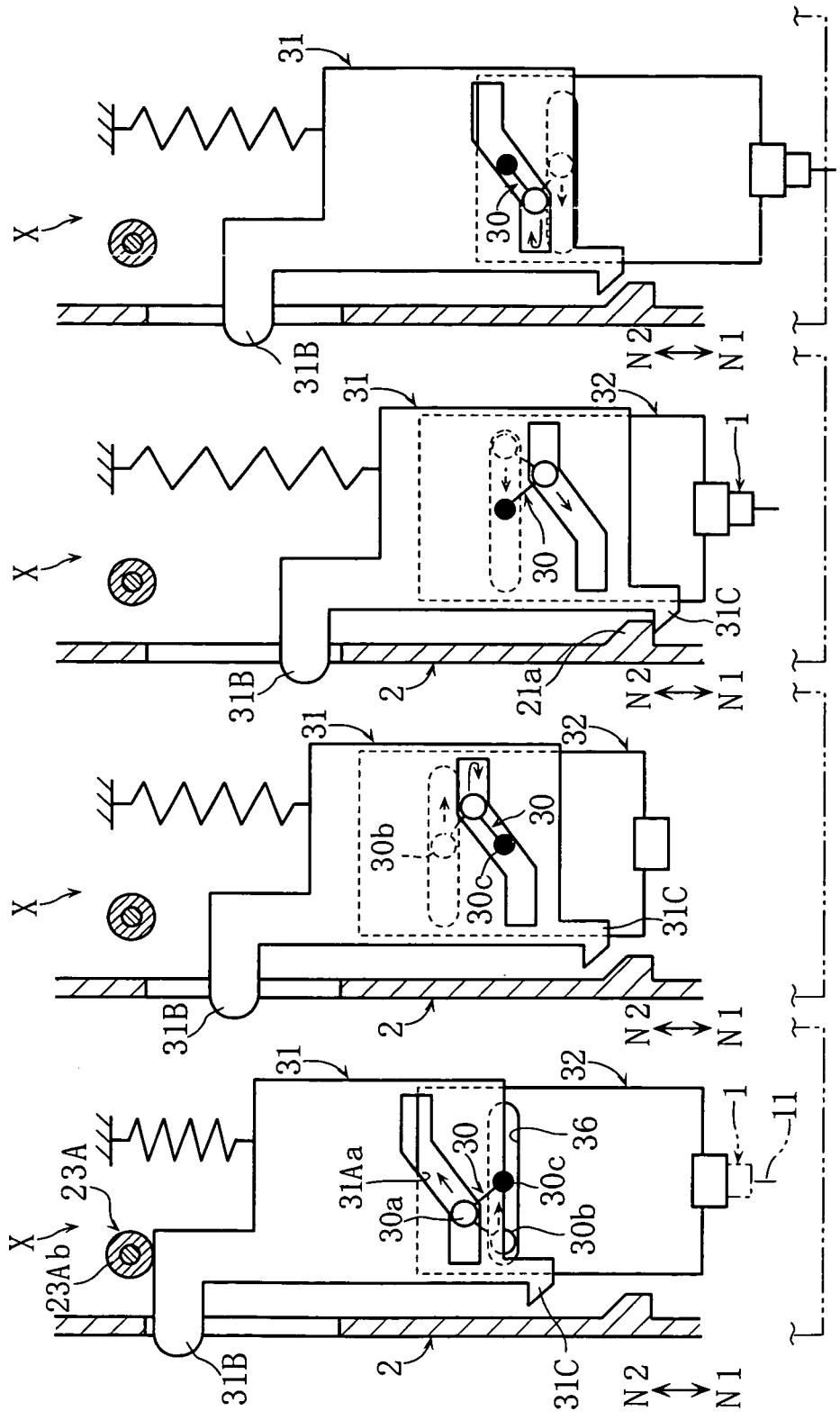

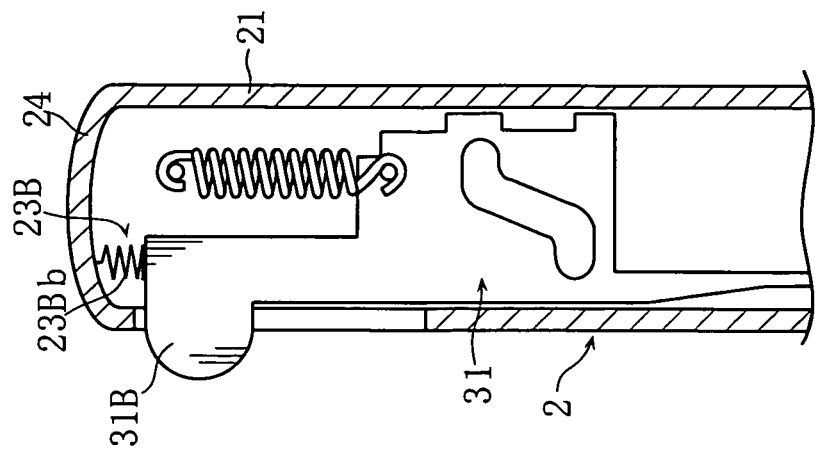
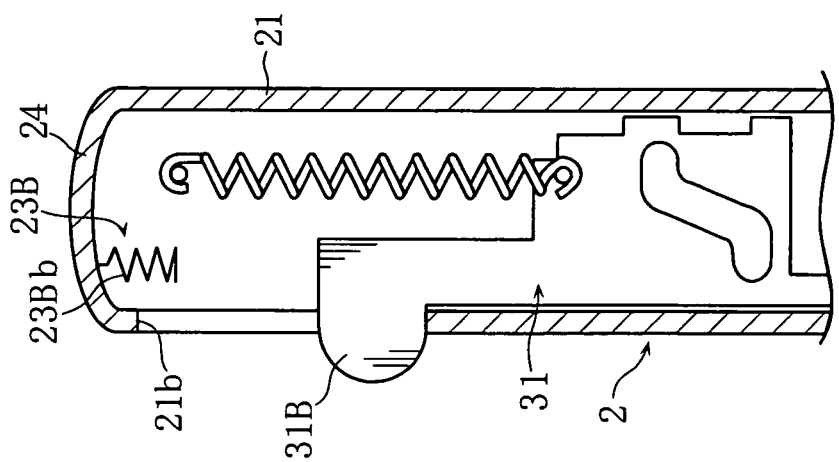

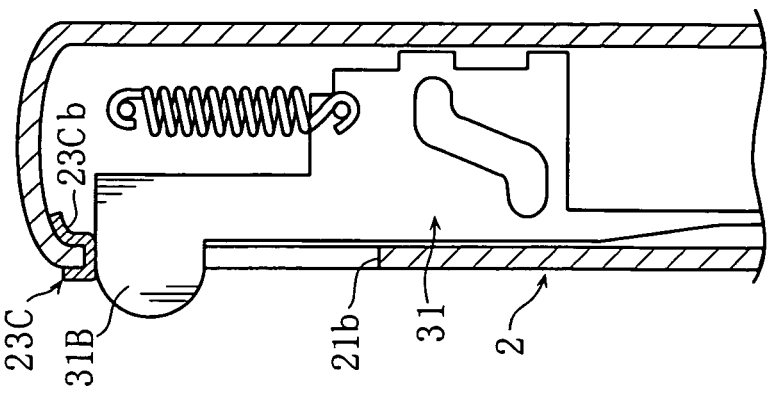
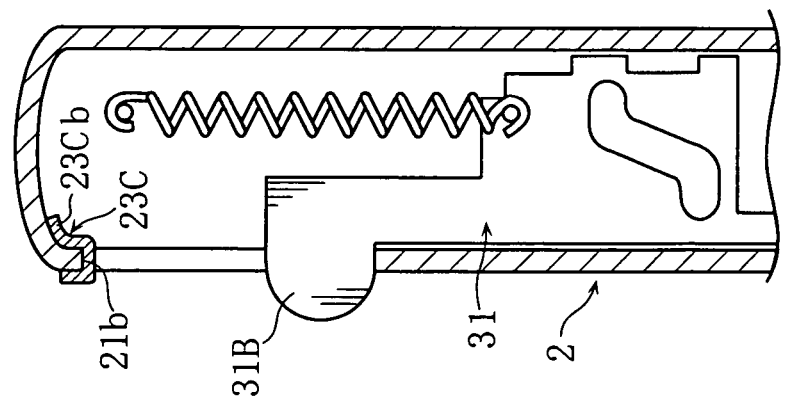

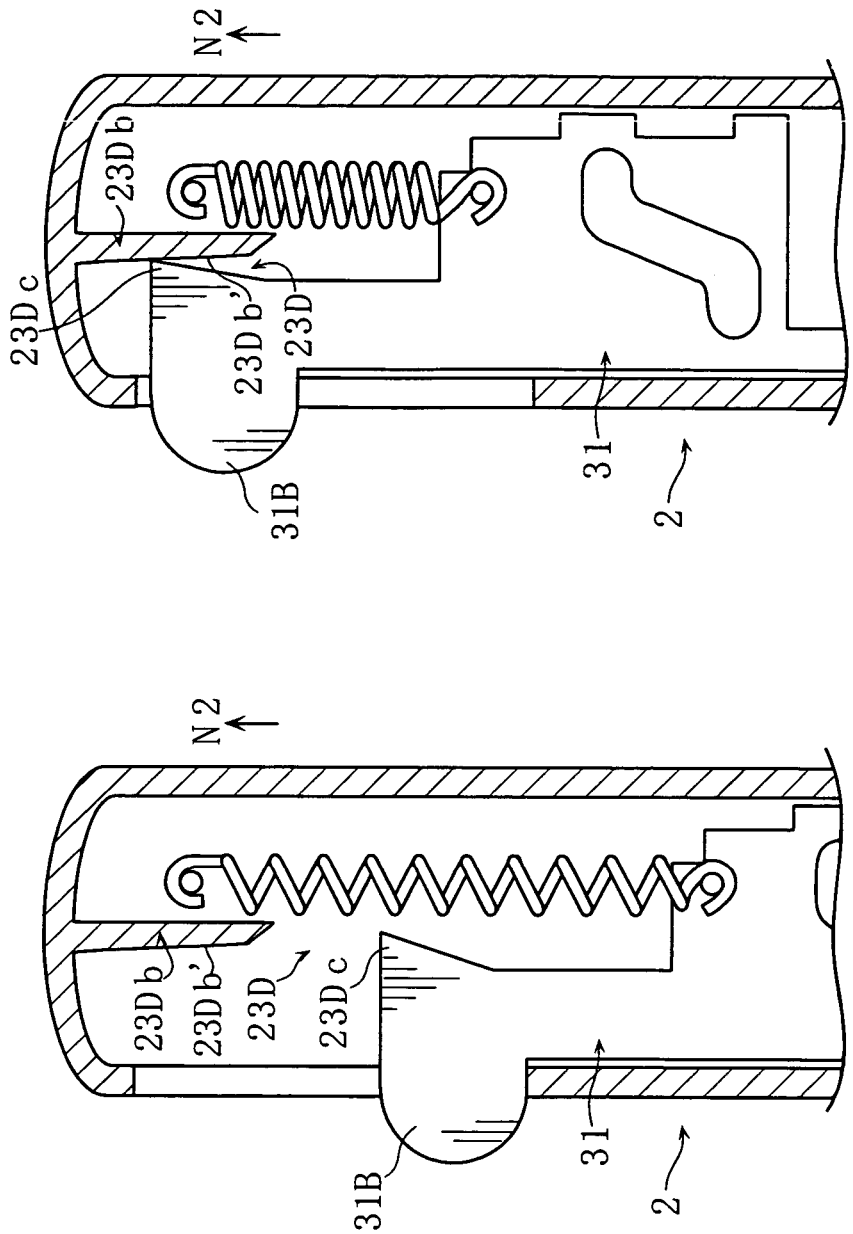

NEEDLE INSERTION DEVICE

TECHNICAL FIELD

The present invention relates to a lancing device that punctures skin by a lancing member to obtain a sample of blood or a tissue.

BACKGROUND ART

An example of the lancing device utilizes a cam mechanism for sticking a lancet into skin (refer to JP-U-64-42010, for example). As shown in FIGS. 15A-15C, the lancing device disclosed in JP-U-64-42010 includes a cam 90 whose rotation is transformed into a reciprocal movement of a lancet supporting portion 91, so that a lancet 92 is moved together with the lancet supporting portion 91 to puncture the skin.

As shown in FIG. 15A, in a standby position of the lancing device 9, the cam 90 is fixed with an urged coil spring 93. A pivot lever 94 is operated to disengage the fixation of the cam 90, as shown in FIGS. 15B and 15C. Then, the cam 90 rotates about a shaft 95. The cam 90 is formed with a v-shaped groove 96, and the groove 96 engages an engaging pin 97 that is formed integral with the lancet supporting portion 91. Thus, when the cam 90 rotates, the engaging pin 97 moves along the groove 96. In this way, the lancet supporting portion 91 reciprocally moves in the puncturing direction N1 and the retreating direction N2 as guided within a sliding hole 98, whereby the lancet 92 reciprocally moves in the puncturing and retreating directions N1, N2 together with the lancet supporting portion 91.

In the lancing device 9, the reciprocal movement of the lancet supporting portion 91 (lancet 92) on puncture operation is stopped by the engaging pin 97 that is brought into contact with the end of the groove 96. Specifically, the engaging pin 97 is moved relative to the groove 96 by the cam 90 that moves due to the restoring force of the coil spring 93. Then, the engaging pin 97 collides against the end of the groove 96 when the cam 90 comes to stop. Therefore, on puncturing, the impact due to the collision of the engaging pin 97 and the end of the groove 96 is transmitted to the skin, and the impact causes pain and discomfort, and thus increase pain on sampling. Further, impact noise due to the collision may intensify the feeling of pain, and combination of the impact noise and the pain may increase discomfort.

DISCLOSURE OF THE INVENTION

An object of the present invention is to provide a lancing device for decreasing pain and discomfort on puncturing.

According to the present invention, there is provided a lancing device that comprises: a first moving member holding a lancing member moved from a standby position to a puncturing position in a puncturing direction, for puncturing a target portion by the lancing member; a second moving member connected to the first moving member, for controlling the movement of the first moving member upon the movement of the second moving member; a housing for accommodating the first and the second moving members, while allowing the movement of the moving members; and an impact absorbing means for absorbing impact that is caused when the first and the second moving members come to stop on puncture operation.

Here, the impact absorbing means absorbs the impact not only at the moment when the first and the second moving members stop, but from when the moving members start to stop.

Preferably, the impact absorbing means includes an elastic member for absorbing the impact by elastic deformation. The elastic member may be made of e.g. polymeric material, typically of rubber or foam (urethane or sponge). The elastic member may also be made of a spring such as a plate spring or a coil spring.

For example, the elastic member is fixed to the housing. Preferably, the housing is provided with a projection for fixing the elastic member, and the elastic member is a ring fitting around the projection. In this case, the elastic member is made of rubber or foam.

Preferably, the elastic member is a coil spring for intervening between the housing and the first or the second moving member, when the first and the second moving members come to stop on puncture operation.

Preferably, the second moving member comprises an operating portion including a portion protruding out of an opening of the housing. In this case, the elastic member is provided at one of the opening or the operating portion, and is made of rubber, foam, or a coil spring.

Preferably, the lancing device according to the present invention further comprises a link connecting the first and the second moving members for moving the first moving members upon the movement of the second moving member. In this case, at least one of the first and the second moving members may be formed with a groove for allowing movement of a shaft of the link. The elastic member may be provided at an end of the groove or at the shaft.

Preferably, the impact absorbing means absorbs the energy of the movement of the first and the second moving members utilizing friction resistance.

Preferably, the impact absorbing means includes an inclined or curved surface provided at a portion at which the housing comes into contact with at least one of the first and the second moving members, when the first and the second moving members come to stop on puncture operation.

Here, the impact absorbing means may include a plurality of inclined surfaces, or a plurality of curved surfaces, or a combination of at least one inclined surface and at least one curved surface. An example of such a surface includes a wave surface.

Preferably, the impact absorbing means includes a lib for contact with the inclined or curved surface, when the first and the second moving members come to stop on puncture operation. The lib is provided at one or both of the first and the second moving members, and the inclined or curved surface is provided at the housing.

Preferably, the second moving member comprises an operating portion including a portion protruding out of an opening of the housing, and the lib may be provided at the operating portion.

Preferably, the lancing device according to present invention further comprises a link connecting the first and the second moving members for moving the first moving members upon the movement of the second moving member. At least one of the first and the second moving members is formed with a groove for allowing movement of a shaft of the link. The impact absorbing means is provided by tapering the end of the groove to form a portion narrower than the shaft in diameter. The shaft is brought into contact with the tapered portion to absorb the energy of the movement of the first and the second moving members.

Preferably, the impact absorbing means includes an elastic member for absorbing impact by elastic deformation and also includes a frictional portion for absorbing the energy of the movement of the first and the second moving members utilizing friction resistance.

Preferably, the frictional portion includes an inclined or curved surface provided at a portion at which the housing comes into contact with at least one of the first and the second moving members, when the first and the second moving members come to stop on puncture operation.

Here, the frictional portion may include a plurality of inclined surfaces, or a plurality of curved surfaces, or a combination of at least one inclined surface and at least one curved surface. An example of such a surface includes a wave surface.

Preferably, the elastic member is a plate spring for contact with the inclined or curved surface, when the first and the second moving members come to stop on puncture operation.

Preferably, the plate spring is movable in a direction across the puncturing direction. The plate spring may include a projection protruding in a direction across the puncturing direction for contact with the inclined or curved surface.

Preferably, the inclined or curved surface is provided at the housing, and the plate spring is provided at the second moving member.

Preferably, advance or reciprocal movement of the second moving member is transformed into reciprocal movement of the first moving member. Specifically, when the second moving member retreats in a direction opposite to the puncturing direction, the first moving member reciprocates in the puncturing direction and then in the direction opposite to the puncturing direction. The present invention may also be applied to a lancing device where rotation of the second moving member is transformed into advance or reciprocal movement of the first moving member.

BRIEF DESCRIPTION OF THE DRAWINGS

FIG. 6 is a pattern diagram illustrating a puncturing operation of the lancing device of FIG. 1.

FIG. 7 is a sectional view illustrating an impact absorbing means of a second embodiment of the present invention.

FIG. 8 is a sectional view illustrating an impact absorbing means of a third embodiment of the present invention.

FIG. 9 is a sectional view illustrating an impact absorbing means of a fourth embodiment of the present invention.

BEST MODE FOR CARRYING OUT THE INVENTION

First through eighth preferred embodiments of the present invention are described below with reference to the accompanying drawings.

A first embodiment of the present invention is described with reference to FIGS. 1-8.

Figure 1:
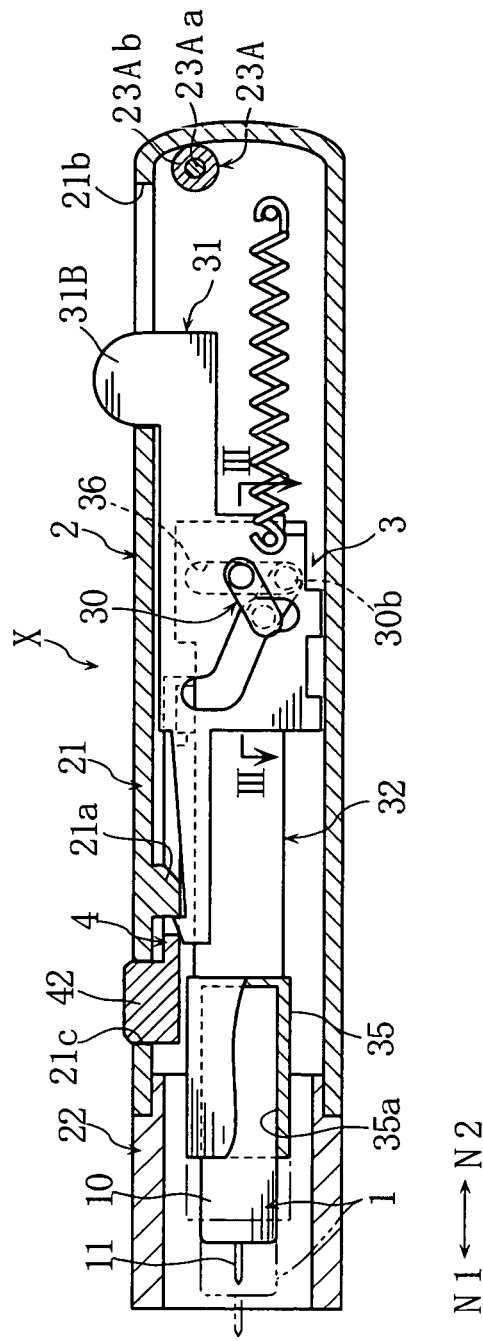
FIG. 1 is a sectional view illustrating a lancing device according to a first embodiment of the present invention.

As shown in FIG. 1, a lancing device X is used for puncturing skin to cause bleeding therefrom, by moving a lancet 1 from a standby position (where the lancet 1 is illustrated by solid lines in the figure) to a puncturing position (where the lancet 1 is illustrated by phantom lines in the figure). The lancing device X includes a housing 2, a lancet moving mechanism 3, and a latch-releasing member 4.

The above-described lancet 1 for puncturing the skin is held in a lancet holder 32 which will be described later, and moves integrally with the lancet holder 32. The lancet 1 includes a body 10 and a lancing needle 11 protruding from the body, and is disposable, for example. The body 10 is tubular and made of a resin, for example. The lancing needle 11 is made of e.g. metal, and is integrated to the body 10 by insert molding. The lancing needle 11 of the lancet 1 may also adhere to the body 10.

The housing 2 defines a space for accommodating various components, and includes first and second sleeves 21, 22.

The first sleeve 21 includes a projection 21a and first and second openings 21b, 21c. The projection 21a engages a moving plate 31 of the lancet moving mechanism 3. The first opening 21b allows movement of an operating portion 31B of the moving plate 31. The second opening 21c allows movement of an end of the latch-releasing member 4.

The first sleeve 21 accommodates an impact absorbing means 23A in the vicinity of the first opening 21b. The impact absorbing means 23A is for contact with the operating portion 31B of the moving plate 31, and includes a projection 23Aa formed in the first sleeve 21 and an elastic member 23Ab held by the projection. The elastic member 23Ab is a ring made of rubber or foam.

Figure 2:
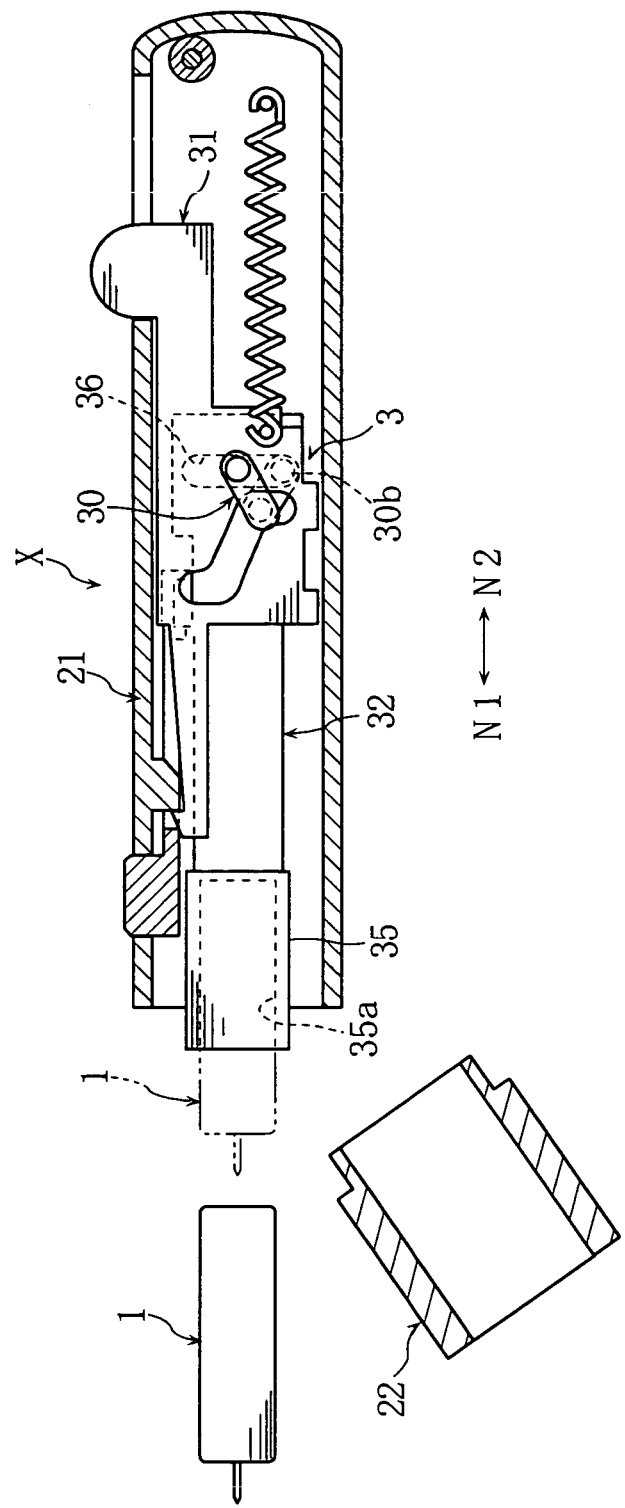
FIG. 2 is a sectional view illustrating the lancing device of FIG. 1 without a second sleeve and a lancet.

The second sleeve 22 is a cylinder including open ends for allowing movement of the lancet holder 32, as described below. As shown in FIGS. 1-2, the second sleeve 22 is attachable to and removable from a tip end of the first sleeve 21. Thus, the lancet 1 can be easily attached to the lancet holder 32 by removing the second sleeve 22 from the first sleeve 21.

Figure 3:
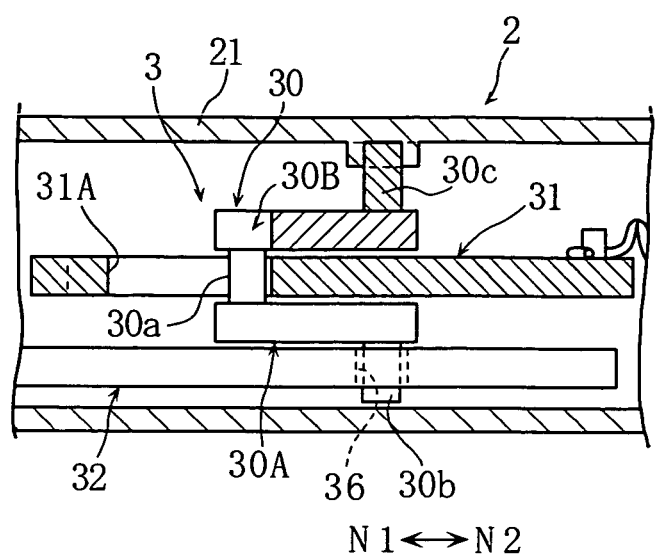
FIG. 3 is a sectional view taken along lines III-III in FIG. 1.

As shown in FIGS. 1-3, the lancet moving mechanism 3 includes a link 30, a moving plate 31, and a lancet holder 32. The lancet moving mechanism 3 transforms reciprocal movement of the moving plate 31 into reciprocal movement of the lancet holder 32 via circular movement of the link 30.

Figure 4:
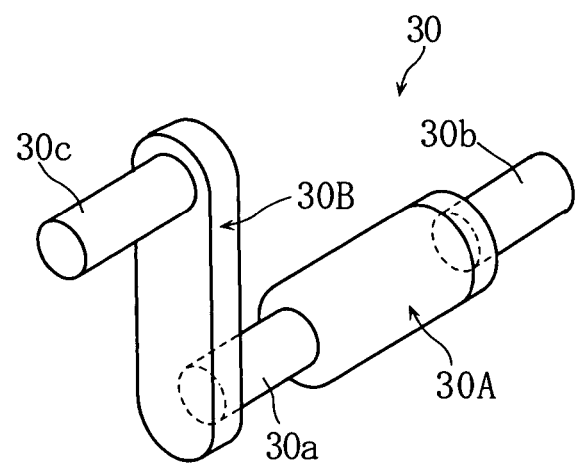
FIG. 4 is an overall perspective view illustrating a link.

The link 30 moves the lancet holder 32 in response to the movement of the moving plate 31. As shown in FIGS. 3 and 4, the link 30 includes a first movable pin 30a, a second movable pin 30b, a fixed pin 30c, a first arm 30A, and a second arm 30B.

As clearly shown in FIG. 3, the first movable pin 30a engaging with the moving plate 31 connects the first arm 30A to the second arm 30B, and movable within a groove 31A of the moving plate 31. The movable pin 30b engaging with the lancet holder 32 is movable within a groove 36 of the lancet holder 32. The fixed pin 30c rotatably attaches the link 30 to the housing 2 (at the first sleeve 21).

Figure 5A:
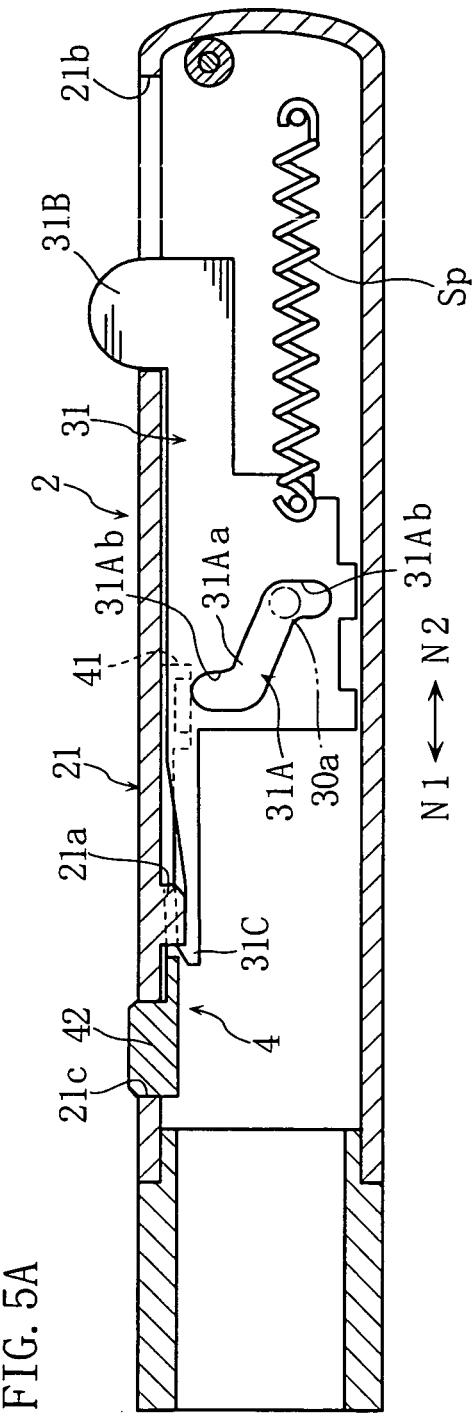
FIG. 5 is a sectional view illustrating an inner structure of the lancing device of FIG. 1, partly omitting its components.
Figure 5B:
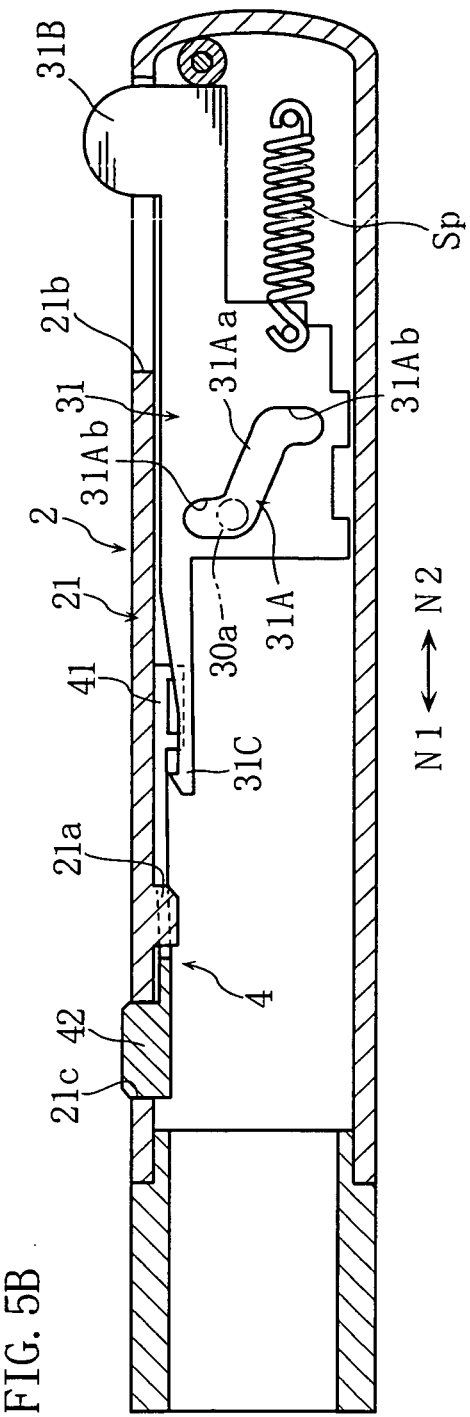

As shown in FIGS. 5A and 5B, the moving plate 31 is movable relative to the housing 2 in a puncturing direction N1 and in a retreating direction N2, and is connected to the housing 2 via a coil spring Sp. The moving plate 31 includes a groove 31A, an operating portion 31B, and a hook 31C.

The groove 31A allows movement of the first movable pin 30a of the link 30 (see FIGS. 3 and 4). The groove 31A includes an inclined portion 31Aa inclined relative to the puncturing and retreating directions N1, N2, and linear portions 31Ab connected to the ends of the inclined portion 31Aa.

The operating portion 31B is used to manually move the moving plate 31. The operation portion 31B partially protrudes beyond the first opening 21b of the housing 2, and moves within the first opening 21b in the puncturing and retreating directions N1, N2.

The hook 31C engages with the projection 21a of the housing 2 for latching the moving plate 31 to the housing 2. As clearly shown in FIG. 5B, when the coil spring Sp of the moving plate 31 is compressed, the hook 31C is in the retreating direction N2 with respect to the projection 21a. On the other hand, as clearly shown in FIG. 5A, when the hook 31C of the moving plate 31 engages with the projection 21a, the coil spring Sp is stretched with a restoring force applied in the retreating direction n2.

As shown in FIGS. 1 and 2, the lancet holder 32 holding the lancet 1 moves the lancet 1, and similarly to the moving plate 31, is movable in the puncturing and retreating direction N1, N2. As shown in FIGS. 1 and 2, the lancet holder 32 includes a holder 35 for holding the lancet 1 and also includes a groove 36 connected with the moving plate 31 via the link 30.

The holder 35 includes a recess 35a having an inner form corresponding to the outer form of the lancet 1. As may be seen from FIGS. 1-3, the groove 36 allows movement of the second movable pin 30b of the link 30 in a direction perpendicular to the puncturing and the retreating directions N1, N2.

As shown in FIGS. 5A and 5B, the latch-releasing member 4 for releasing the moving plate 31 from latching to the housing 2 is suitably flexible and includes an end 41 fixed to the housing 2 (the first sleeve 21). Thus, the other end 42 of the latch-releasing member 4 is pivotable about the end 41. The end 42 is exposed at the second opening 21c of the housing 2 and is movable within the second opening 21c. Thus, when the end 42 is pushed down, the end 42 moves inwardly of the housing 2, thereby releasing the moving plate 31 (the hook 31C) from engagement with the projection 21a of the housing 2 (the first sleeve 21).

Next, description is made as to the use and the operation of the lancing device X. Note that in the beginning, as shown in FIG. 6A, the moving plate 31 retreats in the retreating direction N2 to the free position (upper dead point), and the first movable pin 30a is positioned at the left end of the inclined portion 31Aa of the groove 31A of the moving plate 31, while the second movable pin 30b is positioned at the left end of the groove 36 of the lancet holder 32.

As shown in FIGS. 1 and 6C, on puncturing skin by the lancing device X, the hook 31C of the moving plate 31 is brought into engagement with the projection 21a of the housing 2, and then the lancet 1 is attached to the lancet holder 32. However, the attachment of the lancet 1 to the lancet holder 32 may be performed before the latching of the moving plate 31 to the housing 2.

As shown in FIGS. 6A-6C, the hook 31C is brought into engagement by moving the operating portion 31B of the moving plate 31 in the puncturing direction N1.

On moving the moving plate 31 in the puncturing direction N1 from the position shown in FIG. 6A, entire link 30 including the second movable pin 30b is rotated clockwise about the fixed pin 30c, and accordingly the lancet holder 32 retreats in the retreating direction N2, as shown in FIGS. 6A and 6B. On moving the moving plate 31 in the puncturing direction N1 further rotated clockwise as shown in FIG. 6C, and accordingly the lancet holder 32 is advanced in the puncturing direction N1. In such an instance, the coil spring Sp is stretched and the moving plate 31 is latched to the housing 2 with a restoring force applied in the retreating direction N2.

On attachment of the lancet 1, the second sleeve 22 is removed from the first sleeve 21 as shown in FIG. 2, so that the holder 35 of the lancet holder 32 is exposed. In this state, the lancet 1 is inserted, at its portion opposite to the lancing needle 11, into the holder 25.

After the completion of the latching of the moving plate 31 as well as the attachment of the lancet 1, the end 42 of the latch-releasing member 4 is pressed down, as shown in FIGS. 5A and 5B, to puncture the skin. When the end 42 is pressed down, the end 42 pivots about the end 41, and the end 42 moves inwardly of the housing 2. Then, the end 42 contacts the hook 31C to release the hook 31C from the engagement with the projection 21a.

Here, the moving plate 31 moves in the retreating direction N2 as the moving plate 31 is urged in the retreating direction N2 as described above, whereby the link 30 rotates clockwise and the lancet holder 32 is advanced in the puncturing direction N1. Thereafter, the moving plate 31 is further moved in the retreating direction N2, whereby the lancet holder 32 retreats in the retreating direction N2. In this way, the lancet holder 32 comes back to the free position where the lancet holder is not latched to the housing 2 as shown in FIG. 6A, whereby the lancing needle 11 of the lancet 1 is removed from the skin.

The movement of the moving plate 31 and the lancet holder 32 is stopped by the elastic member 23Ab of the impact absorbing means 23A that comes into contact with the operating portion 31B of the moving plate 31. Specifically, the elastic member 23Ab absorbs the energy of the movement of the moving plate 31 to be stopped. Thus, the lancing device X can regulate the impact, the impact noise and the vibration on puncturing, thereby reducing the pain or discomfort of a user.

In the present embodiment, the impact absorbing means 23A is provided at a portion which comes into contact with the operating portion 31B of the moving plate 31. However, the impact absorbing means 23A may be provided at other portion, as far as it comes into contact with any portion of the moving plate 31 when the moving plate 31 moves on puncture operation.

Next, second to eighth embodiments of the present invention are described below with reference to FIGS. 7 to 13. In these figures, elements identical to those described in the first embodiment are given the same reference numbers.

In the second embodiment, as shown in FIGS. 7A and 7B, an impact absorbing means 23B is designed as a coil spring 23Bb. The coil spring 23Bb is provided at an upper wall 24 of the housing 2 (first sleeve 21).

In this structure, the operating portion 31B of the moving plate 31 is brought into contact with the coil spring 23Bb on puncture operation. Then, the coil spring 23Bb is elastically deformed to absorb the energy of the movement of the moving plate 31, thereby stopping the movement of the moving plate 31.

An impact absorbing means, similar to the impact absorbing means 23B may be provided by an elastic material other than the coil spring such as rubber or foam fixed to the upper wall of the housing, or may be provided by an elastic material such as the coil spring fixed to the moving plate 31.

In a third embodiment, as shown in FIGS. 8A and 8B, an impact absorbing means 23C is designed as an elastic member 23Cb provided at the upper end of the first opening 21b of the housing 2. The elastic member 23Cb may be made of various materials, such as rubber or foam. Of course, a spring such as a coil spring may be used as the elastic member.

In this structure, the operating portion 31B of the moving plate 31 is brought into contact with the elastic member 23Cb on puncture operation. Then, the elastic member 23Cb is elastically deformed to absorb the energy of the movement of the moving plate 31, thereby stopping the movement of the moving plate 31.

In the present embodiment, the elastic member may be fixed to the moving plate 31.

In a fourth embodiment, as shown in FIGS. 9A and 9B, an impact absorbing means 23D utilizes the resistance for absorbing the energy of movement.

The impact absorbing means 23D includes a lib 23Dc provided at an end of the moving plate 31 and an interference wall 23Db provided on an inner surface of the housing 2. The interference wall 23Db for contact with the lib 23Dc includes an inclined surface 23Db' inclined relative to the operating portion 31B.

In this structure, as the moving plate 31 moves in the N2 direction, the transfer resistance between the lib 23Dc and the interference surface 23Db' is increased, thereby gradually absorbing the energy of the movement of the moving plate 31.

The surface of the interference wall 23Db for contact with the lib 23Dc is not limited to the inclined surface, but may be a curved face. The lib may be provided at the housing 2, while a member similar to the interference wall 23Db may be provided at the moving plate 31.

Figure 10A:
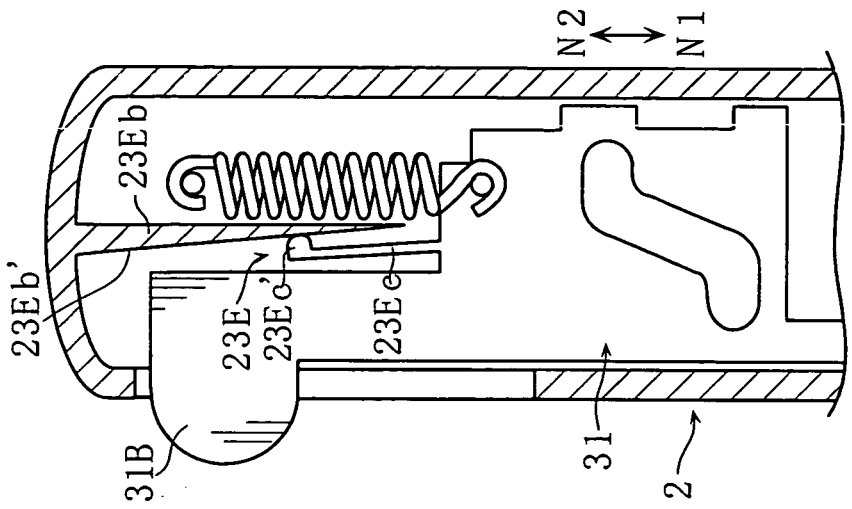
FIG. 10 is a sectional view illustrating an impact absorbing means of a fifth embodiment of the present invention.
Figure 10B:
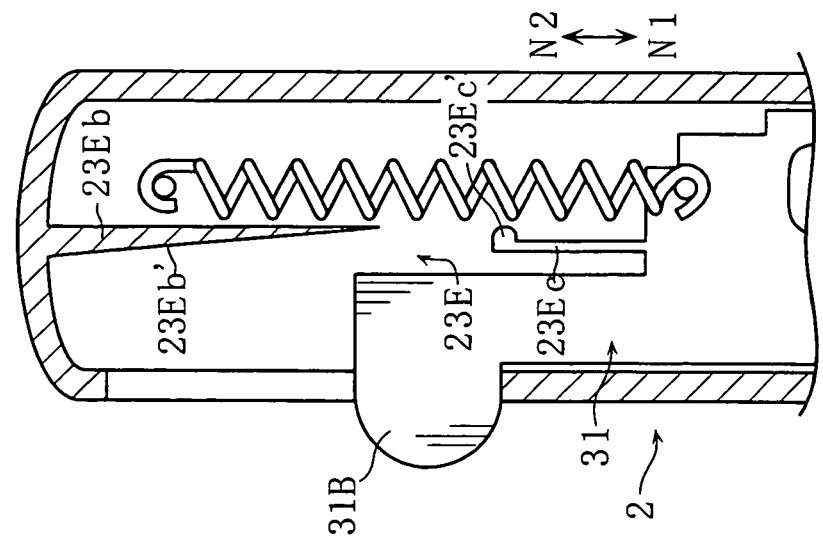

In a fifth embodiment, as shown in FIGS. 10A and 10B, an impact absorbing means 23E is designed to absorb the energy of movement by the transfer resistance and the elastic deformation.

The impact absorbing means 23E includes a plate spring 23Ec provided at the moving plate 31 and an interference wall 23Eb provided on the inner surface of the housing 2. The plate spring 23Ec is pivotable in a direction perpendicular to the moving direction of the moving plate 31 (N1, N2 directions) and includes a projection 23Ec' for contact with the interference wall 23Eb. On the other hand, the interference wall 23Eb includes an inclined surface 23Eb' inclined relative to the operating portion 31B of the moving plate 31, for contact with the projection 23Ec'.

In the impact absorbing means 23E, as the moving plate 31 moves in the N2 direction on puncturing, the transfer resistance between the projection 23Ec' and the inclined surface 23Eb' is increased, and the plate spring 23Ec is elastically deformed, thereby gradually absorbing the energy of the movement of the moving plate 31.

The plate spring may be provided at the housing, while the inclined surface for contact with the plate spring may be provided at the moving plate.

In the first to fifth embodiments, the energy of movement is absorbed by the impact absorbing means 23A-23E that is brought into contact with the moving plate 31. However, the energy of the movement may be absorbed by a similar impact absorbing means that is brought into contact with the lancet holder 32 (see FIG. 1). In this structure, such impact absorbing means for contact with the lancet holder may be replaced with the above impact absorbing means for contact with the moving plate, or may be used together with the impact absorbing means for contact with the moving plate.

Figure 11A:
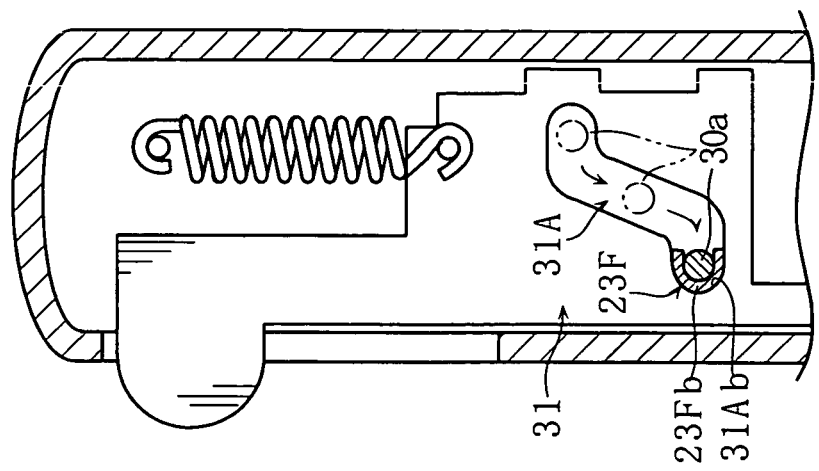
FIG. 11 is a sectional view illustrating an impact absorbing means of a sixth embodiment of the present invention.
Figure 11B:
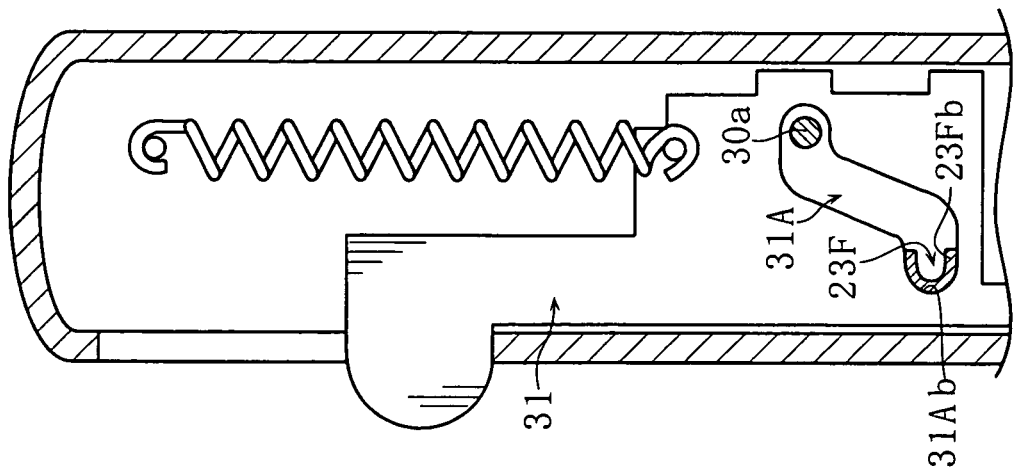

In a sixth embodiment, as shown in FIGS. 11A and 11B, an impact absorbing means 23F is provided at the groove 31A of the moving plate 31. The impact absorbing means 23F includes an elastic member 23Fb positioned at the linear portion 31Ab of the groove 31A.

In this structure, the first movable pin 30a of the link 30 (see FIG. 1) is brought into contact with the elastic member 23Fb on puncturing, thereby stopping the movement of the moving plate 31.

Figure 12:
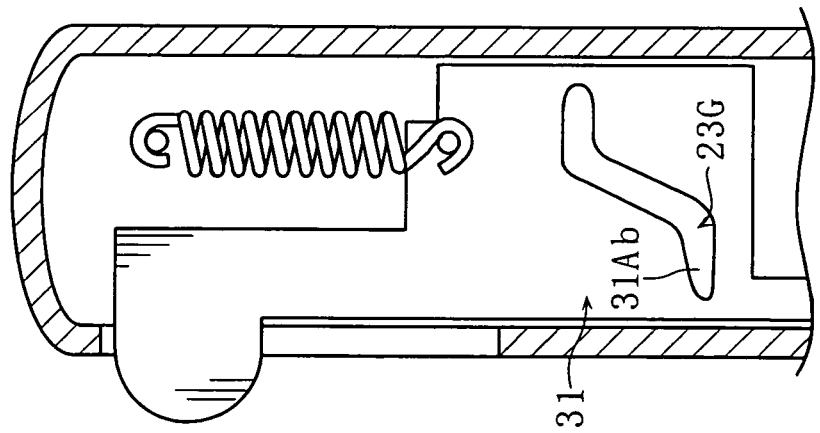
FIG. 12 is a sectional view illustrating an impact absorbing means of a seventh embodiment of the present invention.

In a seventh embodiment, as shown in FIG. 12, an impact absorbing means 23G is provided by utilizing the linear portion 31Ab of the moving plate 31. Specifically, The impact absorbing means 23G is provided by forming the linear portion 31Ab to be narrower as proceeding to its end.

In this structure, the energy of the movement of the moving plate 31 is gradually absorbed as the first movable pin 30a of the link 30 (see FIG. 1) moves in the linear portion 31Ab, thereby stopping the moving plate 31.

Figure 13:
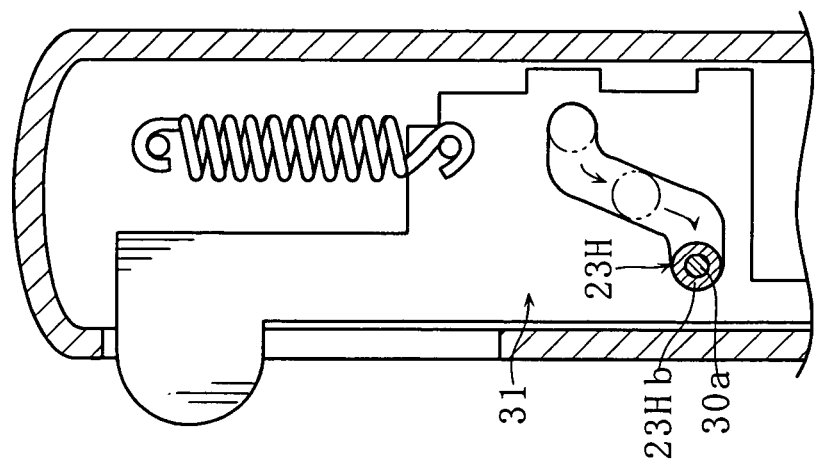
FIG. 13 is a sectional view illustrating an impact absorbing means of an eighth embodiment of the present invention.

In an eighth embodiment, as shown in FIG. 13, an impact absorbing means 23H is provided at the first movable pin 30a of the link 30 (see FIG. 1). The impact absorbing means 23H includes an elastic member 23Hb held at the first movable pin 30a. The elastic member 23Hb is a ring made of rubber or foam, for example.

In this structure, the elastic member 23Hb at the first movable pin 30a of the link 30 (see FIG. 1) is brought into contact with the edge of the groove 31A on puncturing, thereby stopping the movement of the moving plate 31.

In the sixth to eighth embodiments, the position of the first movable pin 30a when stopping the moving plate 31 is variable. For example, the moving plate 31 may be stopped right after the first movable pin 30a turns round at the end of the linear portion 31Ab of the groove 31A. In such a case, the moving plate 31 is slowed down when the first movable pin 30a is brought into contact with the impact absorbing means 23F, 23G, 23H, and then the moving plate 31 is stopped after the first movable pin 30a turns round.

The impact absorbing means 23F-23H of the sixth to eighth embodiments may be used together with the above-described impact absorbing means 23A-23E. An impact absorbing means similar to the impact absorbing means 23F-23H may be provided at the groove 36 of the lancet holder 32 (see FIG. 1). In such a case, the impact absorbing means at the lancet holder 32 may be replaced with the impact absorbing means at the moving plate, or may be used together with the impact absorbing means at the moving plate.

Figure 14A:
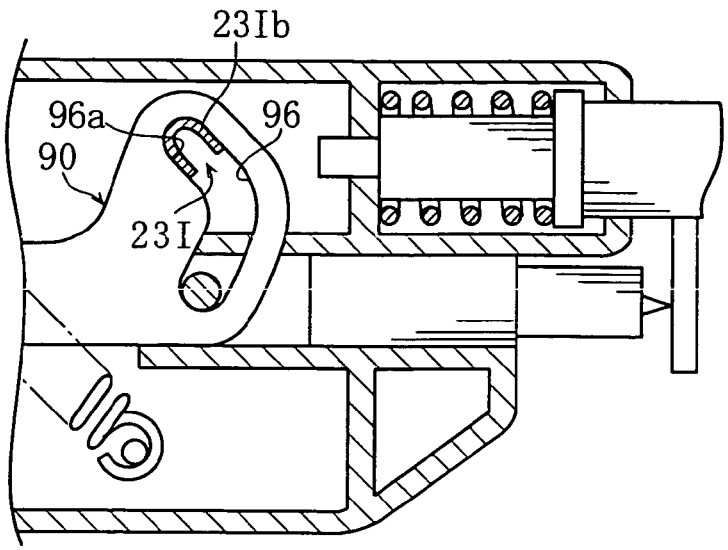
FIG. 14 is a sectional view illustrating the impact absorbing means according to the present invention applied to another lancing device.
Figure 14B:
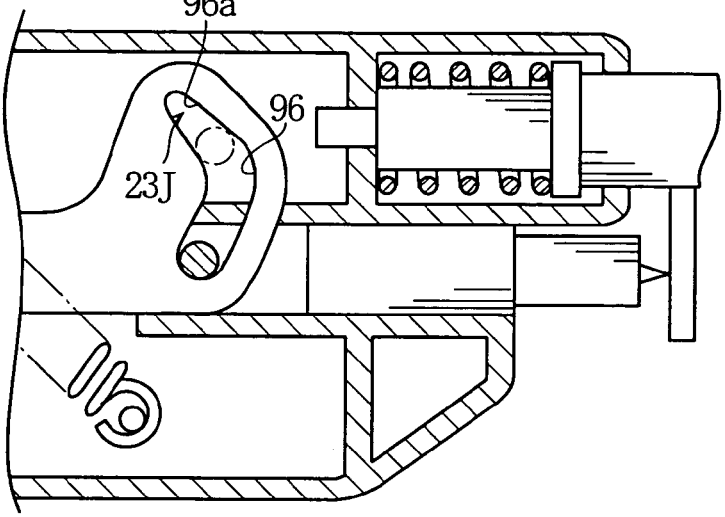
Figure 14C:
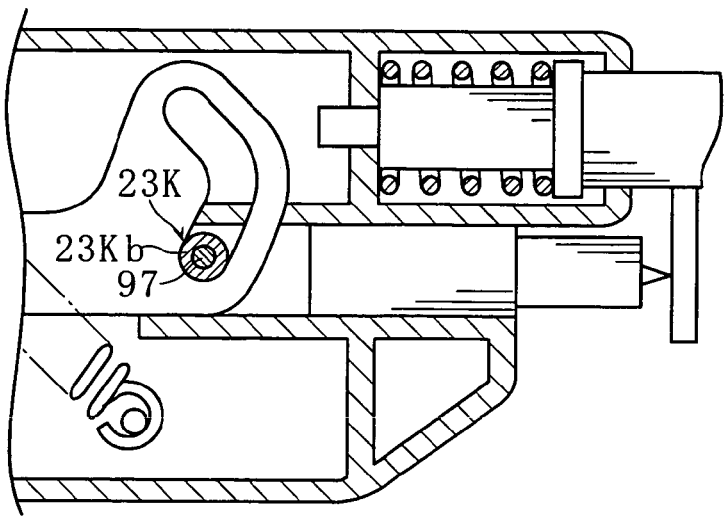
Figure 15A:
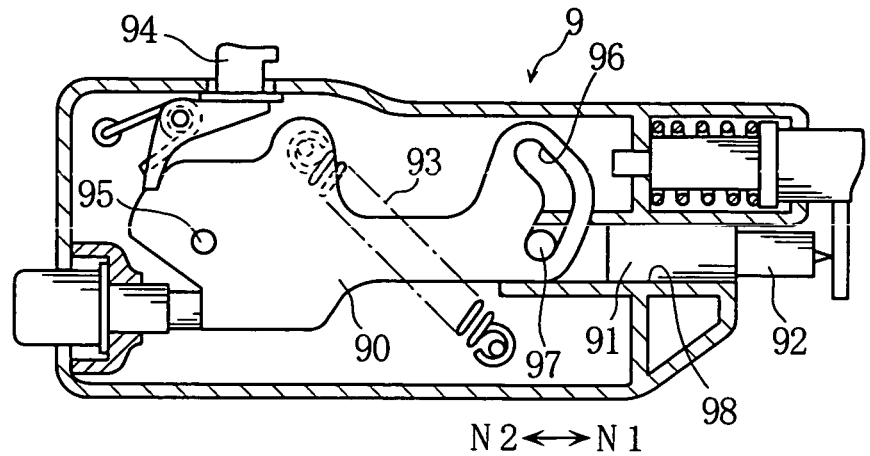
FIG. 15 is a sectional view illustrating an example of a conventional lancing device.
Figure 15B:
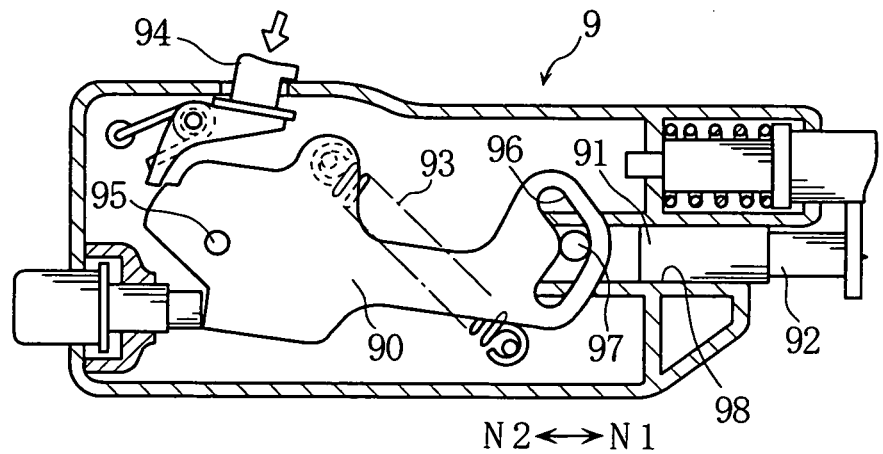
Figure 15C:
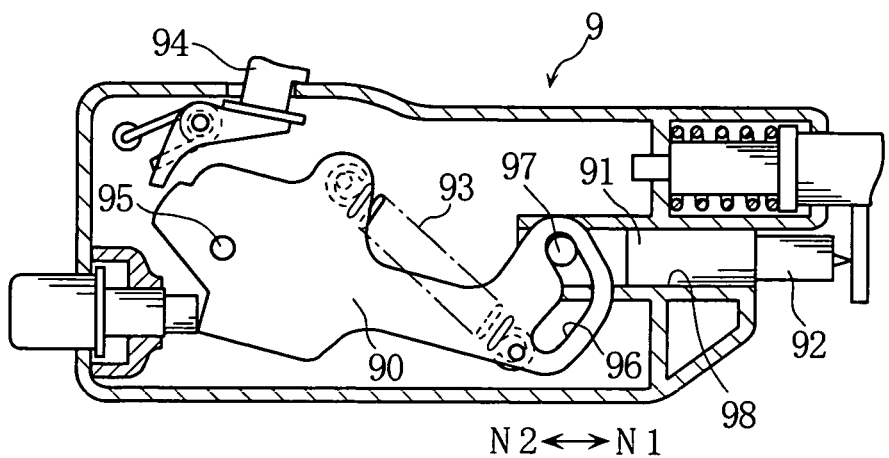

Of course, the present invention is not limited to the impact absorbing means 23A-23H illustrated in the first to eighth embodiments, but a differently designed impact absorbing means may be provided. Further, the impact absorbing means may be applied to a lancing device other than the lancing device described in the first embodiment. For example, the impact absorbing means may be applied to a lancing device 9 described as a conventional example with reference to FIGS. 15A-15C. Specifically, as shown in FIG. 14A, an impact absorbing means 23I may be provided by positioning an elastic member 23Ib at the end 96a of the groove 96 of the cam 90. As shown in FIG. 14B, an impact absorbing means 23J may be provided by forming the end 96a of the groove 96 to be narrower as proceeding to its end. As shown in FIG. 14C, an impact absorbing means 23K may be provided by fitting an elastic member 23Kb around the ring-shaped engaging pin 97. Further, the lancing device 9 may be provided with various impact absorbing means which is brought into contact with the cam 90 (see FIG. 14A) to absorb the energy of movement, similarly to the impact absorbing means 23A-23E illustrated in the first to fifth embodiments, or may be provided with another impact absorbing means.

The present invention may further be applied to a lancing device in which a lancet holder is connected to a rotating member rotating around an axis elongated in the puncturing direction, and the lancet holder moves in response to the movement of the rotating member.

The invention claimed is:

1. A lancing device comprising:
a first moving member holding a lancing member that is moved from a standby position to a puncturing position in a puncturing direction for puncturing a target portion by the lancing member;
a second moving member connected to the first moving member for controlling the movement of the first moving member, the second moving member being moved between a retreated position and an advanced position;
a housing for accommodating the first and second moving members while allowing the movement of the first and second moving members;
a latch mechanism for latching the second moving member onto the housing at the advanced position;
a movement converting mechanism for converting retreating movement of the second moving member from the advanced position toward the retreated position into advancing movement of the lancing member from the standby position toward the puncturing position; and
an impact absorber provided separately from the latch mechanism, the impact absorber being spaced from the second moving member when the second moving member is latched onto the housing by the latch mechanism, the impact absorber coming into contact with the second moving member in the retreating movement toward the retreated position for absorbing impact that is caused when the first and second moving members come to stop during a puncturing operation.

2. The lancing device according to claim 1, wherein the impact absorber includes an elastic member for absorbing the impact by elastic deformation.

3. The lancing device according to claim 2, wherein the elastic member is fixed to the housing.

4. The lancing device according to claim 3, wherein the housing is provided with a projection for fixing the elastic member, the elastic member being a ring fitting around the projection.

5. The lancing device according to claim 4, wherein the elastic member is made of rubber or foam.

6. The lancing device according to claim 2, wherein the elastic member is a coil spring intervening between the housing and the first or the second moving member, when the first and the second moving members come to stop during a puncturing operation.

7. The lancing device according to claim 2, wherein the second moving member comprises an operating portion including a portion protruding out of an opening of the housing,
the elastic member being provided at one of the opening and the operating portion.

8. The lancing device according to claim 2, wherein the movement converting mechanism comprises a link connecting the first and the second moving members for moving the first moving member upon movement of the second moving member,
wherein at least one of the first and the second moving members is formed with a groove for allowing movement of a shaft of the link.

9. The lancing device according to claim 8, wherein the elastic member is provided at the shaft.

10. The lancing device according to claim 1, wherein the impact absorber absorbs the energy of the movement of the first and the second moving members utilizing friction resistance.

11. The lancing device according to claim 10, wherein the impact absorber includes an inclined or curved surface provided at a portion at which the housing comes into contact with at least one of the first and the second moving members, when the first and the second moving members come to stop during a puncturing operation.

12. The lancing device according to claim 11, wherein the impact second moving member includes a lib for contact with the inclined or curved surface, when the first and the second moving members come to stop during a puncturing operation.

13. The lancing device according to claim 12, wherein the lib is provided on both of the first and the second moving members, the inclined or curved surface being provided at the housing.

14. The lancing device according to claim 13, wherein the second moving member comprises an operating portion including a portion protruding out of an opening of the housing,
the lib being provided at the operating portion.

15. The lancing device according to claim 1, wherein reciprocal movement of the second moving member is transformed into reciprocal movement of the first moving member.

16. The lancing device according to claim 1, wherein the movement converting mechanism comprises a fixed pin fixed to the housing, a first link extending from the fixed pin, a first movable pin connected to the first link, a second link extending from the first movable pin, a second movable pin connected to the second link, a first groove formed in the second moving member and having an inclined portion for movably receiving the first movable pin, and a second groove formed in the first moving member for movably receiving the second movable pin.

17. A lancing device comprising:
a first moving member holding a lancing member moved from a standby position to a puncturing position in a puncturing direction for puncturing a target portion by the lancing member;
a second moving member connected to the first moving member for controlling the movement of the first moving member;
a housing for accommodating the first and the second moving members while allowing the movement of the moving members;
a movement converting mechanism for converting retreating movement of the second moving member away from the puncturing position into advancing movement of the lancing member to the puncturing position; and
an impact absorber that comes into contact with the second moving member in the retreating movement for absorbing impact that is caused when the first and the second moving members come to stop during a puncturing operation;
wherein the movement converting mechanism comprises a fixed pin fixed to the housing, a first link extending from the fixed pin, a first movable pin connected to the first link, a second link extending from the first movable pin, a second movable pin connected to the second link, a first groove formed in the second moving member and having an inclined portion for movably receiving the first movable pin, and a second groove formed in the first moving member for movably receiving the second movable pin.

* * * * *